United States Patent [19]

Takada et al.

[11] Patent Number: 5,312,927

[45] Date of Patent: May 17, 1994

[54] PREPARATION OF IMIDAZOLES

[75] Inventors: Susumu Takada, Kawanishi; Makoto Adachi, Ikoma, both of Japan

[73] Assignee: Shionogi & Co., Inc., Osaka, Japan

[21] Appl. No.: 106,550

[22] Filed: Aug. 16, 1993

[30] Foreign Application Priority Data

Aug. 18, 1992 [JP] Japan .................................. 4-219078

[51] Int. Cl.$^5$ .................. C07D 233/56; C07D 233/58; C07D 233/64
[52] U.S. Cl. ............................. 548/335.1; 548/335.5; 548/336.1; 548/341.1; 548/342.5; 548/343.1; 548/343.5; 548/345.1; 548/346.1; 548/235; 548/247; 546/193; 546/194; 546/200; 546/210; 546/272; 546/278; 544/122; 544/370
[58] Field of Search ............... 548/335.1, 335.5, 336.1, 548/341.1, 342.5, 343.1, 343.5, 345.1, 346.1; 546/193, 194, 200, 210, 272, 278; 544/122, 370

[56] References Cited

U.S. PATENT DOCUMENTS 4,377,696 3/1983 Graf .................................. 548/335.1
4,409,389 10/1983 Bellas et al. ...................... 548/335.1

OTHER PUBLICATIONS

March, *Advanced Organic Chemistry-Reactions, Mechanisms and Structure*, 4th Edition, John Wiley & Sons, New York, 1992, p. 896.

*Primary Examiner*—Richard L. Raymond
*Assistant Examiner*—Brian Bembenick
*Attorney, Agent, or Firm*—Wenderoth, Lind & Ponack

[57] ABSTRACT

The present invention relates to preparation of imidazoles which are useful as pharmaceutical and agricultural chemicals. Specifically, the present invention relates to a process for preparing imidazoles of the formula (I):

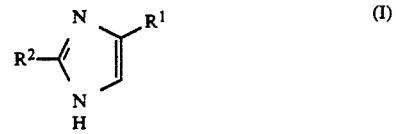

which comprises conducting condensation among an α,α-dihaloaldehyde compound of the formula (II):

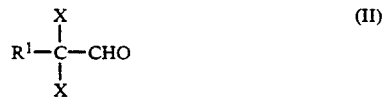

an aldehyde compound of the formula: $R^2$—CHO and aqueous ammonia.

4 Claims, No Drawings

PREPARATION OF IMIDAZOLES

FIELD OF THE INVENTION

The present invention relates to a novel process for preparation of imidazoles. In more particular, the present invention relates to a novel process for preparation of imidazoles which involves a condensation reaction among an α,α-dihaloaldehyde compound, an aldehyde compound, and aqueous ammonia.

Derivatives of the imidazoles which are obtained by the process of the present invention may be used as a useful starting material in preparations of pharmaceutical and agricultural chemicals, and so on.

THE PRIOR ART

Processes for preparing imidazoles which are useful as starting materials of pharmaceutical and agricultural chemicals have been described in the following publications:

a) R. Weidenhagen, et al., Ber., 68 1953 (1935);

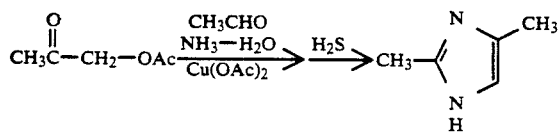

b) W. Longenback, et al., Ann., 585 68 (1954);

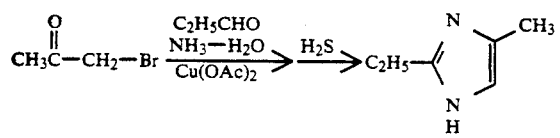

c) K. Bodendorf, et al., Arch. Pharm., 298 293 (1965);

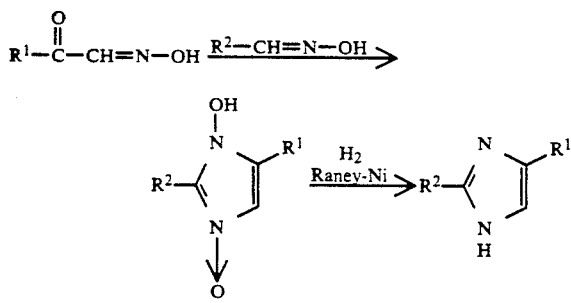

d) M. L. Scheinbaum, et al., Tetrahedron Lett., 2205 (1971);

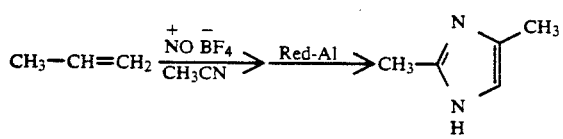

However, the processes described in the publications have various drawbacks. For instance, the above reactions (a) and (b) require the use of Cu(OAc)$_2$, which contains a heavy metal, and hydrogen sulfide, which is a poisonous gas, and therefore, the reactions may be dangerous to laboratory workers. The reaction (c) often requires tedious procedures to prepare a ketoaldoxime, which is used as a starting material. In the reaction (d), nitrosonium tetrafluoroborate is expensive.

As stated above, the previously known processes have some disadvantages, and therefore, there is a demand of developing a new process for preparing imidazoles which is free from the above disadvantages.

DESCRIPTION OF THE PRESENT INVENTION

The present invention relates to a process for preparing imidazoles, which comprises condensating an α,α-dihaloaldehyde compound, an aldehyde compound, and aqueous ammonia at room temperature or at an elevated temperature.

Specifically, the present invention relates to a process for preparing imidazoles of the formula (I):

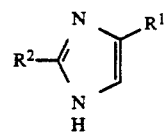

which comprises conducting condensation among an α,α-dihaloaldehyde compound of the formula (II):

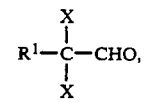

an aldehyde compound of the formula: R$^2$—CHO and aqueous ammonia;

in which X is halogen and R$^1$ is (1) hydrogen;

(2) alkyl group;

(3) a haloalkyl group of the formula: Y—(CH$_2$)$_m$— wherein Y is chloro or bromo, and m is an integer of from 2 to 6;

(4) acyloxyalkyl group of the formula: R$^3$—O—(CH$_2$)$_n$— wherein n is an integer of from 2 to 6, and R$^3$ is an acyl group;

(5) a cyanoalkyl group of the formula: NC—(CH$_2$)$_p$— wherein p is an integer of from 1 to 6;

(6) a cycloalkyl group;

(7) a group of the formula: R$^4$—S—(CH$_2$)$_q$— wherein R$^4$ is lower alkyl or phenyl group, and q is an integer of from 1 to 5;

(8) a group of the formula: CF$_3$—(CH$_2$)$_r$— wherein r is an integer of from 0 to 5;

(9) a group of the formula:

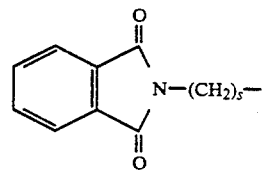

wherein s is an integer of from 1 to 5;

(10) an aralkyl group of the formula:

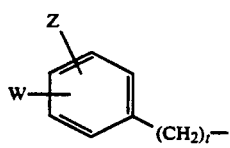

wherein W and Z are independently hydrogen, halogen, alkyl, alkoxy, acetylamino, cyano, or nitro group, or a group: —COOR$^5$ wherein R$^5$ is lower alkyl group, or W and Z taken together may form alkylenedioxy group, and t is an integer of from 1 to 5; or

(11) an aryl group of the formula:

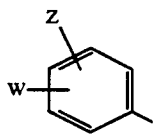

wherein
W and Z have the same meaning as defined above;
R$^2$ has the same meaning as R$^1$ or R$^2$ may represent a group selected from the group consisting of

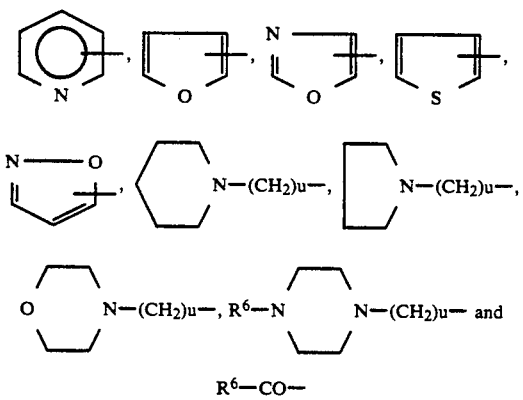

wherein R$^6$ is hydrogen, lower alkyl, alkoxy or phenyl, and u is an integer of from 1 to 5.

In the specification, the term "alkyl" refers to a straight or branched $C_1$–$C_{10}$ alkyl group or $C_3$–$C_6$ cycloalkyl-($C_1$–$C_5$) alkyl such as methyl, ethyl, n-propyl, i-propyl, n-butyl, i-butyl, t-butyl, and the like alkyl groups. In the term "acyloxyalkyl group", "acyl" refers to $C_2$–$C_7$ aliphatic acyl such as acetyl, propionyl, butyryl, and $C_7$–$C_{11}$ arylcarbonyl such as benzoyl, toluoyl, and so on. "Cycloalkyl group" refers to $C_3$–$C_6$ cycloalkyl such as cyclopropyl, cyclobutyl, cyclopentyl, and cyclohexyl. "Lower alkyl" refers to a straight or branched $C_1$–$C_6$ alkyl group such as methyl, ethyl, n-propyl, i-propyl, n-butyl, i-butyl, t-butyl, and so on.

The term "alkoxy" refers to $C_1$–$C_6$ alkyloxy such as methoxy, ethoxy, propoxy, isopropoxy, butoxy, isobutoxy, tertbutoxy, pentoxy, hexyloxy, and so on. The term "halogen" refers to chlorine, bromine, iodine, or fluorine. The term "alkylenedioxy" refers to $C_1$–$C_4$ alkylenedioxy such as methylenedioxy, ethylenedioxy, and so on.

The above condensation reaction can be carried out in an inert organic solvent. The inert organic solvent includes methanol, ethanol, isopropyl alcohol, tetrahydrofuran, acetonitrile, N,N-dimethylformamide, dichloromethane, 1,2-dichloroethane, benzene, toluene, and so on. Alternatively, desired imidazoles can also be prepared by reacting an acetal of α,α-dihaloaldehyde compound and an aldehyde compound with an aqueous ammonia in the presence of ammonium chloride. The starting material, α,α-dihaloaldehyde compound is synthesized in accordance with the teaching in published literatures such as N. Schamp et al., Synthesis, 455 (1975), N. Schamp et al., Bull. Soc. Chim. Belg., 89 441 (1980), F. Bellesia et al., J. Chem. Research (s). 16 (1983), and R. G. Pews et al., Synth. Commun., 15 977 (1985).

The process of the present invention is free from previously-mentioned disadvantages, and the present invention provides a simple process for the preparation of imidazoles. In particular, the process of the present invention is advantageous in the preparation of 2,4-di-substituted imidazoles. 2,4-Di-substituted imidazoles are useful as starting materials of medicaments, and particularly, they are expected to be starting materials for an anti-HIV agent.

The following examples are provided to further illustrate the process of the present invention. Such examples are representative only, and should not be construed as limiting the scope of the invention in any respect.

EXAMPLE

EXAMPLE 1

4-Isopropyl-2-methylimidazole

A mixture consisting of 3.10 g of 2,2-dichloroisovaleraldehyde and 1.76 g of acetaldehyde was cooled in an ice-water, and to the mixture was added 27 ml of concentrated aqueous ammonia, and then the resulting mixture was stirred for 66 hours at room temperature. The product was extracted with methylene chloride, and the extract was washed with water, and dried over anhydrous magnesium sulfate. The solvent was evaporated to yield 2.52 g of a crude product, which was dissolved in 10 ml of isopropyl alcohol. To the resulting solution was added 10 ml of a solution of 1.80 g of oxalic acid in isopropyl alcohol to precipitate crystals. The crude crystals (3.72 g) was recrystallized from methanol/isopropyl alcohol to yield 3.50 g of crystals (yield: 82%).

Mp: 161°–162° C.

Elementary Analysis (for $C_7H_{12}N_2 \cdot C_2H_2O_4$): Theory: C, 50.46; H, 6.59; N, 13.08 (%); Found: C, 50.20; H, 6.61; N, 13.29 (%).

H-NMR (CDCl$_3$) [for free base] δ: 7.8 (1H, br NH), 6.60 (1H, m, C$_5$—H), 2.89 (1H, m, J=7 Hz, C$\underline{H}$(Me)$_2$), 2.37 (3H, s, C$_2$—CH$_3$), 1.24 (6H, d, J=7 Hz, CH(M$\underline{e}$)$_2$).

EXAMPLE 2

2-Phenyl-4-n-propylimidazole

A mixture consisting of 1.55 g of 2,2-dichloroisovaleraldehyde, 1.27 g of benzaldehyde, and 8 ml of acetonitrile was cooled in an ice-water, and to the mixture was added 13.5 ml of concentrated aqueous ammonia, and then the resulting mixture was stirred for 66 hours at room temperature. The product was extracted with methylene chloride, and the extract was washed with water, dried over anhydrous magnesium sulfate, and evaporated to yield a crude product. The crude product was chromatographed using 30 g of silica gels, thereby contaminants which were eluted with 5% acetonitrile/methylene chloride were removed, and fractions which were eluted with 50% acetonitrile/methylene chloride were collected. The collected fractions were evaporated to yield 1.24 g of the residue, which was recrystallized from methylene chloride/ether to yield 0.947 g of crystals (yield: 51%).

Mp: 155°–156° C.

Elementary Analysis (for $C_{12}H_{14}N_2$): Theory: C, 77.38; H, 7.58; N, 15.04 (%); Found: C, 77.57; H, 7.79; N, 15.00 (%).

H-NMR (CDCl$_3$) δ: 7.26–7.86 (5H, m, Ph), 6.84 (1H, s, C$_5$—H), 7.7 (1H, br NH), 2.58 (2H, t, J=7 Hz, CH$_2$CH$_2$CH$_3$), 1.65 (2H, m, J=7 Hz, CH$_2$CH$_2$CH$_3$), 0.93 (3H, t, J=7 Hz, CH$_2$CH$_2$CH$_3$).

EXAMPLE 3

4-Benzyl-2-methylimidazole

A mixture consisting of 2.03 g of phenyl-2,2-dichloropropione aldehyde, 0.88 g of acetaldehyde, and 10 ml of acetonitrile was cooled in an ice-water, and to the mixture was added 13.5 ml of concentrated aqueous ammonia, and then the resulting mixture was stirred for 66 hours at room temperature. Then, the mixture was stirred in an oil bath at 60° C. for additional 3 hours. The solvent of acetonitrile was evaporated in vacuo to yield the oil, which was dissolved in ether, and the resulting solution was extracted with diluted hydrochloric acid. The aqueous extract was made basic with aqueous ammonia, and then, the solution was extracted with methylene chloride, and the extract was washed with water, dried over anhydrous magnesium sulfate, and evaporated off. The crude residue was chromatographed using 30 g of alumina, thereby contaminants which were eluted with methylene chloride were removed, and fractions which were eluted with ethyl acetate were collected. The collected fractions were evaporated to yield 1.04 g of the residue, which was dissolved in 10 ml of isopropyl alcohol. To the solution was added a solution of 544 mg of oxalic acid in 5 ml of isopropyl alcohol to precipitate 1.38 g of crystals (yield: 53%).

Mp: 162°–163° C.

Elementary Analysis (for $C_{11}H_{12}N_2 \cdot C_2H_2O_4$): Theory: C, 59.53; H, 5.38; N, 10.68 (%); Found: C, 59.28; H, 5.43; N, 10.61 (%).

H-NMR (CDCl$_3$) [for free base] δ: 7.14 (5H, m, Ph), 6.55 (1H, s, C$_5$—H), 5.53 (1H, br, NH), 3.88 (3H, s, C$_2$—CH$_3$).

EXAMPLES 4–16

Various imidazoles were prepared according to the procedure as defined above. Conditions of the reactions and data of the resulting compounds are shown in the following table 1.

TABLE 1

$$R^1\underset{X}{\overset{X}{-}}C-CHO \xrightarrow[\text{solvent}]{R^2-CHO} R^2\underset{\underset{H}{N}}{\overset{\overset{R^1}{N}}{\diagdown}}$$

| Exa. | R¹,X (g) | R² (g) | con. A (ml) | sol. (ml) | reaction temp. (°C.) | time (hr) | yield (g) | (%) | molecular formula | m.p. (°C.) | EA (%) Found (Theory) | | ¹H-NMR(CDCl₃) δ(J,Hz) for free base |
|---|---|---|---|---|---|---|---|---|---|---|---|---|---|
| 4 | i-Pr,Cl 1.55 | CH₃ 0.88 | 13.5 | none | r.t. | 24 | 1.63 | 76 | C₇H₁₂N₂·C₂H₂O₄ | 120–121 | C. H. N. | 50.26(50.46) 6.61(6.59) 13.00(13.08) | 7.24(1H, br.s, NH), 6.61(1H, s, C₅—H), 2.52(2H, t, J=7Hz, CH₂CH₂CH₃), 2.37(3H, s, C₂—CH₃), 1.64(2H, m, J=7Hz, CH₂CH₂CH₃), 0.95(3H, t, J=7Hz, CH₂CH₂CH₃) |
| 5 | n-Pr,Cl 1.55 | PhCH₂ 1.44 | 13.5 | CH₃CN 8 | r.t. | 66 | 1.72 | 59 | C₁₃H₁₆N₂·C₂H₂O₄ | 158–159 | C. H. N. | 62.14(62.06) 6.37(6.25) 9.55(9.65) | 7.19–7.36(5H, m, ph), 6.60(1H, s, C₅—H), 5.6(1H, br, NH), 4.03(2H, s, CH₂ph), 2.50(2H, t, J=7Hz, CH₂CH₂CH₃), 1.62(2H, m, J=7Hz, CH₂CH₂CH₃), 0.94(3H, t, J=7Hz, CH₂CH₂CH₃) |
| 6 | H,Cl 1.31 | CH₃ 0.88 | 13.5 | none | r.t. | 19 | 0.416 | 51 | C₄H₆N₂ | 144–145 | | | 9.02(1H, br.s, NH), 6.96(2H, s, C₄—H and C₅—H), 2.43(3H, s, C₂—CH₃) |
| 7 | H,Cl 1.31 | ph 1.27 | 13.5 | CH₃CN 5 | r.t. | 19 | 0.483 | 34 | C₉H₈N₂ | 151 | | | 7.33–7.41 and 7.85–7.90(5H, m, ph), 7.14(2H, s, C₄—H and C₅—H), 6.95(1H, br.s, NH) |
| 8 | phCH₂,Cl 2.03 | H 0.60 | 13.5 | CH₃CN 10 | r.t. | 67 | 0.903 | 57 | C₁₀H₁₀N₂ | 81–82 | C. H. N. | 75.92(75.92) 6.43(6.37) 17.76(17.71) | 7.49(1H, s, C₂—H), 7.15–7.33(5H, m, ph), 6.72(1H, s, C₅—H), 5.63(1H, br.s, NH), 3.95(2H, s, CH₂ph) |
| 9 | phCH₂,Cl 2.03 | CH₃OCH₂ 1.48 | 13.5 | none | 55 | 24 | 1.21 | 41 | C₁₂H₁₄N₂O·C₂H₂O₄ | 91–92 | C. H. N. | 57.62(57.53) 5.37(5.52) 9.57(9.59) | 7.16–7.34(5H, m, ph), 6.67(1H, s, C₅—H), 4.48(2H, s, CH₂OCH₃), 3.93(2H, s, CH₂ph), 3.38(3H, s, OCH₃) |
| 10 | phCH₂,Cl 2.03 | 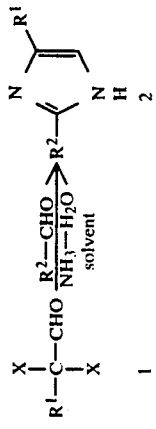 CH₃O— 2.72 | 13.5 | none | 55 | 24 | 0.583 | 22 | C₁₇H₁₆N₂O | 198–199 | C. H. N. | 77.38(77.24) 6.10(6.10) 10.59(10.60) | 6.98 and 7.81(4H, d, J=9Hz, arom H), 7.29(1H, s, C₅—H), 7.27(5H, m, ph), 3.78(2H, s, CH₂ph), 3.34(3H, s, OCH₃)(in DMSO) |
| 11 | i-Pr,Cl 1.55 | Cl— 2.81 | 13.5 | CH₂Cl₂ 10 | r.t. | 72 | 0.730 | 33 | C₁₂H₁₃N₂Cl | 192–193 | C. H. N. Cl. | 65.56(65.30) 5.87(5.94) 12.69(12.70) 16.34(16.07) | 7.30 and 7.72(4H, d, J=9Hz, arom H), 6.83(1H, s, C₅—H), 2.97(1H, m, J=7Hz, CH(CH₃)₂), 1.29(6H, d, J=7Hz, CH(CH₃)₂) |

TABLE 1-continued $$R^1-\underset{\underset{X}{|}}{\overset{\underset{X}{|}}{C}}-CHO \xrightarrow[\text{solvent}]{R^2-CHO, NH_3-H_2O} R^2\underset{\underset{H}{|}}{\overset{N}{\diagup}}\underset{\underset{2}{|}}{\overset{R^1}{\diagdown}}$$

| Exa. | R¹, X (g) | R² (g) | con. A (ml) | sol. (ml) | reaction temp. (°C.) | time (hr) | yield (g) (%) | molecular formula | m.p. (°C.) | EA (%) Found (Theory) | ¹H-NMR(CDCl₃) δ(J,Hz) for free base |
|---|---|---|---|---|---|---|---|---|---|---|---|
| 12 | n-Pr,Cl 1.55 | NCCH₂CH₂ 1.66 | 13.5 | none | r.t. | 66 | 1.04 / 64 | C₉H₁₃N₃ | 96-97 | C: 66.28(66.22) H: 8.01(8.03) N: 25.76(25.75) | 7.45(1H, br.s, NH), 6.69(1H, s, C₅—H), 3.04(2H, t, J=7Hz, CH₂CH₂CN), 2.80(2H, t, J=7Hz, CH₂CH₂CN), 2.54(2H, t, J=7Hz, CH₂CH₂CH₃), 1.64(2H, m, J=7Hz, CH₂CH₂CH₃), 0.96(3H, t, J=7Hz, CH₂CH₂CH₃) |
| 13 | n-Pr,Cl 1.55 | (4-methylpyridin-yl) 2.14 | 13.5 | CH₂Cl₂ 10 | r.t. | 24 | 0.897 / 48 | C₁₁H₁₃N₃ | 160-161 | C: 70.74(70.56) H: 7.09(7.00) N: 22.35(22.44) | 8.55(2H, m, C₂'—H and C₆'—H), 8.2(1H, br, NH), 7.77(2H, m, C₃'—H and C₅'—H), 6.97(1H, s, C₅—H), 2.63(2H, t, J=7Hz, CH₂CH₂CH₃), 1.68(2H, m, J=7Hz, CH₂CH₂CH₃), 0.95 and 0.96(3H, t, J=7Hz, CH₂CH₂CH₃) |
| 14 | i-Pr,Cl 1.55 | (4-nitrophenyl) 1.81 | 13.5 | CH₂Cl₂ 16 | r.t. | 24 | 0.428 / 19 | C₁₂H₁₃N₃O₂ | 181-182 | C: 62.47(62.32) H: 5.81(5.67) N: 18.08(18.17) | 7.94-8.24(4H, m, arom H), 6.96(1H, s, C₅—H), 5.5(1H, br, NH), 3.20(1H, m, J=7Hz, CH(CH₃)₂), 1.32(6H, d, J=7Hz, CH(CH₃)₂) |
| 15 | C₂H₅,Br 2.30 | CH₃ 0.88 | 13.5 | CH₂Cl₂ 10 | r.t. | 21 | 1.40 / 70 | C₆H₁₀N₂·C₂H₂O₄ | 145-146 | C: 47.90(47.99) H: 5.88(6.04) N: 13.95(13.99) | 6.61(1H, s, C₅—H), 5.88(1H, br.s, NH), 2.59(2H, q, J=8Hz, CH₂CH₃), 2.37(3H, s, C₂—CH₃), 1.22(3H, t, J=8Hz, CH₂CH₃) |
| 16 | C₂H₅,Br 2.30 | CH₃CH₂ 1.16 | 13.5 | CH₂Cl₂ 10 | r.t. | 21 | 1.34 / 63 | C₇H₁₂N₂·C₂H₂O₄ | 95-96 | C: 50.45(50.46) H: 6.61(6.59) N: 13.05(13.08) | 6.62(1H, s, C₅—H), 5.96(1H, br.s, NH), 2.73(2H, q, J=8Hz, C₂—CH₂CH₃), 2.60(2H, q, J=8Hz, C₅—CH₂CH₃), 1.30(3H, t, J=8Hz, C₂—CH₂CH₃), 1.22(3H, t, J=8Hz, C₅—CH₂CH₃) |

Exa.; Example Number
con. A; concentrated aqueous ammonia
sol.; solvent
temp.; temperature
EA; Elementary Analysis

EXAMPLE 17

4-n-Butyl-imidazole

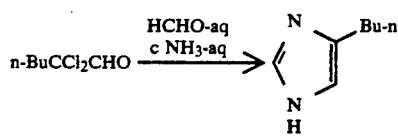

A mixture consisting of 1.69 g of 2,2-dichloro-n-hexyl aldehyde and 1.62 g of 37% aqueous formaldehyde was cooled in an ice-water, and to the mixture was added 13.5 g of concentrated aqueous ammonia, and then the mixture was stirred for 22.5 hours at room temperature. The product was extracted with methylene chloride, and the extract was washed with water, dried over anhydrous magnesium sulfate, and evaporated to yield 1.26 g of a crude product, which was dissolved in 5 ml of isopropyl alcohol. To the solution was added 5 ml of a solution of 0.90 g of oxalic acid in isopropyl alcohol to precipitate crystals. The crude crystals (1.49 g) were recrystallized from methanol/isopropyl alcohol to yield 1.39 g of the oxalate (mp: 182°-184° C.).

A solution of the oxalate dissolved in water was made basic with aqueous sodium bicarbonate, and the solution was extracted with methylene chloride, washed with water, dried over anhydrous potassium carbonate, and evaporated to yield 0.907 g of the title compound as white crystals (yield: 73.0%).

Mp: 42°-45° C.

$^1$H-NMR (CDCl$_3$) δ: 7.99 (1H, br, NH), 7.55 (1H, s, C$_2$—H), 6.78 (1H, s, C$_5$—H) 2.61 (2H, t, J=8 Hz, —CH$_2$—), 1.37 and 1.63 (4H, m, —CH$_2$—), 0.92 (3H, t, J=7 Hz, CH$_3$).

What is claimed is:

1. A process for preparing imidazoles of the formula (I):

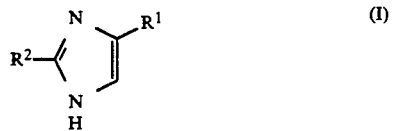

in which R$^1$ is (1) hydrogen; (2) alkyl group; (3) a haloalkyl group of the formula: Y—(CH$_2$)$_m$— wherein Y is chloro or bromo, and m is an integer of from 2 to 6; (4) an acyloxyalkyl group of the formula: R$^3$—O—(CH$_2$)$_n$— wherein n is an integer of from 2 to 6, and R$^3$ is an acyl group; (5) a cyanoalkyl group of the formula: NC—(CH$_2$)$_p$— wherein p is an integer of from 1 to 6; (6) a cycloalkyl group; (7) a group of the formula: R$^4$—S—(CH$_2$)$_q$— wherein R$^4$ is lower alkyl or phenyl group, and q is an integer of from 1 to 5; (8) a group of the formula: CF$_3$—(CH$_2$)$_r$— wherein r is an integer of from 0 to 5; (9) a group of the formula:

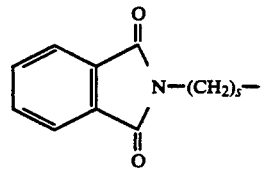

wherein s is an integer of from 1 to 5; (10) an aralkyl group of the formula:

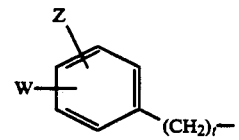

wherein W and Z are independently hydrogen, halogen, alkyl, alkoxy, acetylamino, cyano, or nitro group, or a group: —COOR$^5$ wherein R$^5$ is lower alkyl, or W and Z, taken together, may form alkylenedioxy group, and t is an integer of from 1 to 5; or (11) an aryl group of the formula:

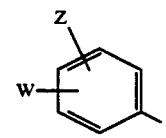

wherein
W and Z have the same meaning as defined above; R$^2$ has the same meaning as R$^1$ or R$^2$ may represent a group selected from the group consisting of

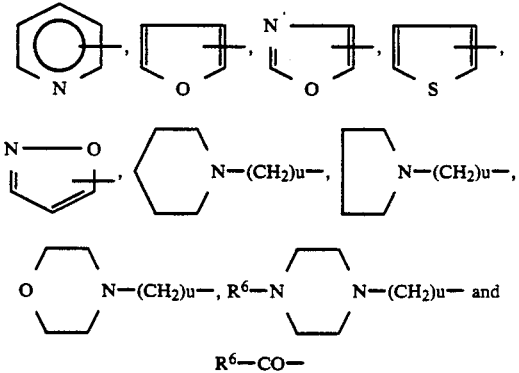

wherein R$^6$ is hydrogen, lower alkyl, alkoxy, or phenyl, and u is an integer of from 1 to 5,
which comprises conducting condensation among an α,α-dihaloaldehyde compound of the formula (II):

$$R^1-\underset{\underset{X}{|}}{\overset{\overset{X}{|}}{C}}-CHO \qquad (II)$$

in which R1 is as defined above, and X is halogen, an aldehyde compound of the formula: R$^2$—CHO in which R$^2$ is as defined above, and aqueous ammonia.

2. The process of claim 1, in which R$^1$ and R$^2$ are independently alkyl group.

3. The process of claim 2, in which R$^1$ and R$^2$ are independently methyl, ethyl, or propyl.

4. The process of claim 1, in which R$^1$ is alkyl group and R$^2$ is hydrogen.

* * * * *